US012685322B2

(12) United States Patent
Frazier

(10) Patent No.: US 12,685,322 B2
(45) Date of Patent: Jul. 21, 2026

(54) LIQUID-HOLDING EDIBLE OBJECT

(71) Applicant: James Frazier, Sturgis, MS (US)

(72) Inventor: James Frazier, Sturgis, MS (US)

( * ) Notice: Subject to any disclaimer, the term of this patent is extended or adjusted under 35 U.S.C. 154(b) by 307 days.

(21) Appl. No.: 18/489,488

(22) Filed: Oct. 18, 2023

(65) Prior Publication Data

US 2025/0000119 A1     Jan. 2, 2025

Related U.S. Application Data

(60) Provisional application No. 63/524,252, filed on Jun. 30, 2023.

(51) Int. Cl.
| | |
|---|---|
| *A23G 3/54* | (2006.01) |
| *A23G 3/34* | (2006.01) |
| *A23G 3/36* | (2006.01) |
| *A23G 3/42* | (2006.01) |
| *A23G 3/48* | (2006.01) |
| *A61K 31/07* | (2006.01) |
| *A61K 31/122* | (2006.01) |
| *A61K 31/355* | (2006.01) |
| *A61K 31/59* | (2006.01) |
| *A61K 33/06* | (2006.01) |
| *C12G 1/00* | (2019.01) |
| *C12G 3/00* | (2019.01) |

(52) U.S. Cl.
CPC ........... *A23G 3/545* (2013.01); *A23G 3/0072* (2013.01); *A23G 3/362* (2013.01); *A23G 3/368* (2013.01); *A23G 3/42* (2013.01); *A23G 3/48* (2013.01); *A61K 31/07* (2013.01); *A61K 31/122* (2013.01); *A61K 31/355* (2013.01); *A61K 31/59* (2013.01); *A61K 33/06* (2013.01); *C12G 1/00* (2013.01); *C12G 3/00* (2013.01)

(58) Field of Classification Search
CPC .................................. A23G 3/545; A23G 3/44
See application file for complete search history.

(56) References Cited

U.S. PATENT DOCUMENTS

| | | | | |
|---|---|---|---|---|
| 5,916,591 | A | * | 6/1999 | Bierdel-Willkommen .................. A61K 9/4858 424/455 |
| 6,258,380 | B1 | * | 7/2001 | Overholt .............. A61K 9/4825 424/455 |
| 2012/0035277 | A1 | * | 2/2012 | Davis ..................... A61K 47/36 514/777 |
| 2017/0258857 | A1 | * | 9/2017 | Philipp ................ A61K 9/4858 |
| 2019/0364924 | A1 | * | 12/2019 | Capdepon ............ A23G 3/0034 |

* cited by examiner

*Primary Examiner* — Mark V Stevens

(74) *Attorney, Agent, or Firm* — brennan, Manna & Diamond, LLC

(57) ABSTRACT

A liquid-holding edible gummy or edible chew for oral consumption by an individual is disclosed. The gummy is a novel, cost-effective, hollow edible that enables users to consume a desired liquid such as an alcohol shot, a medicine, and more without using conventional bottles, cans, and more. The gummy includes a housing made of a gelling substance and the housing encloses a central cavity which holds a liquid. When the gummy is bitten or chewed, the liquid comes out from the cavity and provides a unique way of consuming the liquid. The gummy can be used as a delivery device for alcohol, medicine, non-alcoholic beverages, etc. The gummy is formed using a mold and the liquid, for example, can be injected inside the cavity through the housing.

16 Claims, 2 Drawing Sheets

100

LIQUID-HOLDING EDIBLE OBJECT

CROSS-REFERENCE TO RELATED APPLICATION

The present application claims priority to, and the benefit of, U.S. Provisional Application No. 63/524,252, which was filed on Jun. 30, 2023 and is incorporated herein by reference in its entirety.

FIELD OF THE INVENTION

The present invention generally relates to the field of edible gummies and candies. More specifically, the present invention relates to a novel liquid-holding edible gummy or edible chew (i.e., chewable) that can hold a liquid therein. The gummy is not solid and has a liquid-filled center wherein the liquid can be alcohol, medicine, non-alcoholic beverages, etc. The gummy can come in different shapes and flavors and can function as a delivery device for different liquids for easy accessibility and consumption. Accordingly, the present disclosure makes specific reference thereto. Nonetheless, it is to be appreciated that aspects of the present invention are also equally applicable to others like applications, devices, and methods of manufacture.

BACKGROUND

By way of background, people like to consume beverages, especially alcoholic shots, non-alcoholic drinks, sodas, and other liquids. However, people often face challenges when trying to consume these liquids when they are travelling. Traditional methods like carrying bottles, cans, or cups can be inconvenient, messy, and may require both hands, making it difficult to multitask while commuting. Also, using conventional means, individuals may end up consuming more quantity of liquids and beverages than they desire. This is due to the lack of proper measuring options and difficulties in controlling the amount of liquid consumed. Commonly, people take medications in the form of tablets or syrups, which can be challenging for them due to difficulties in swallowing or unpleasant taste. This can also act as a deterrent to taking necessary medications.

Gummy candies are popular because people enjoy the act of chewing and swallowing them. However, traditional gummies are often made with sugar and do not offer any additional functionality beyond being a sweet treat. People desire an improved gummy that can hold a beverage such as alcoholic shots, non-alcoholic beverages, sodas, and even medicinal liquids therein for easy and measured consumption by individuals.

Therefore, there exists a long felt need in the art for an improved gummy that offers a more convenient and mess-free way to consume liquids, beverages, and medicines. There is also a long felt need in the art for a liquid-holding edible gummy or edible chew that prevents overconsumption and enables for more precise dosing of alcohol shots and medications. Additionally, there is a long felt need in the art for a liquid-filled gummy that can serve as an alternative and more palatable way to take medications. Moreover, there is a long felt need in the art for an improved gummy that offers an additional functionality in delivering various liquids stored therein, making the gummy more useful. Further, there is a long felt need in the art for a liquid-filled gummy that can hold any liquid therein. Furthermore, there is a long felt need in the art for a gummy that is edible and holds a liquid inside thereof without any leakage. Finally, there is a long felt need in the art for a gummy filled with liquids that overcomes the problems of consuming beverages and medications in a fun and convenient way.

The subject matter disclosed and claimed herein, in one embodiment thereof, comprises a liquid-filled edible gummy or edible chew for use as a delivery device for a liquid for oral consumption by an individual. The gummy comprises a housing made of 60-80% gelatin, 2-5% sweetener, 4-5% flavoring substance, 1-4% preservative, 4-8% supplement, and 5-6% natural coloring and a central cavity enclosed by the housing. The cavity is filled with a liquid, wherein the liquid can be one of water, juice, alcohol shot, and non-alcoholic liquid. The liquid remains in a non-solidified form inside the gummy.

In this manner, the liquid-holding edible gummy, edible chew, or chewable of the present invention accomplishes all of the forgoing objectives and provides users with a gummy filled with liquids and offers a novel solution to the problems of consuming beverages and medications. The gummy provides a fun and convenient way to enjoy alcoholic and non-alcoholic drinks, sodas, and even medicinal liquids, giving users more control over their consumption and a unique experience.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a chewable gummy dosage for oral administration. The gummy dosage includes a liquid filled therein and has a soft and chewy exterior surface. The liquid can be any liquid such as water, fruit drinks, alcohol, and more.

In yet another embodiment, a liquid-filled edible object is disclosed. The object is configured for oral consumption and includes a liquid component, wherein the liquid component can be an alcoholic drink or a non-alcoholic drink, and a chewy housing formed of a gelling substance such as gelatin, the housing has a central cavity for storing the liquid component therein.

In a further embodiment of the present invention, a liquid-holding edible gummy or edible chew for use as a delivery device for a liquid for oral consumption by an individual comprises a housing made of 60-80% gelatin, 2-5% sweetener, 4-5% flavoring substance, 1-4% preservative, 4-8% supplement, and 5-6% natural coloring and a central cavity enclosed by the housing, the cavity storing a liquid, wherein the liquid can be one of water, juice, alcohol shot, and non-alcoholic liquid.

In yet a further embodiment of the present invention, a method for producing an edible gummy or edible chew with a liquid-filled center is described. The method comprising the steps of mixing ingredients to form a uniform and homogeneous mixture, wherein the ingredients comprise at least gelatin, sweeteners, flavorings, at least one color, heating the mixture in a heating furnace to form a thick and sticky liquid, using different molds for the edible gummy or edible chew, wherein each mold comprises a central cavity for forming a hollow center in the edible object, and pouring the sticky liquid into the mold, injecting a desired liquid, selected from alcohol, medicine, or the like, into the hollow center of the edible object, and cooling and solidifying the filled edible objects, and removing the solidified objects from the molds.

The liquid-holding edible gummy or edible chew of the present invention offers a fun and flavorful alternative to traditional gummies and provides a burst of a liquid such as a fruity treat, an alcoholic shot, or a medicinal liquid when bitten into, adding an extra dimension to the candy-eating experience.

In a further embodiment, the gummy can be used as a supplement and a source of Vitamins and calcium.

In yet another embodiment, the gummy holds a volume of liquid from about 5 ml to about 50 ml of alcohol liquid or non-alcohol liquid.

The advantage of the liquid-holding edible gummy or edible chew of the present invention is that it offers a novel and practical way for individuals to consume beverages, including alcoholic and non-alcoholic drinks. The versatility in flavors, shapes, and liquid content enables a customizable and enjoyable experience for consumers.

Numerous benefits and advantages of this invention will become apparent to those skilled in the art to which it pertains upon reading and understanding of the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
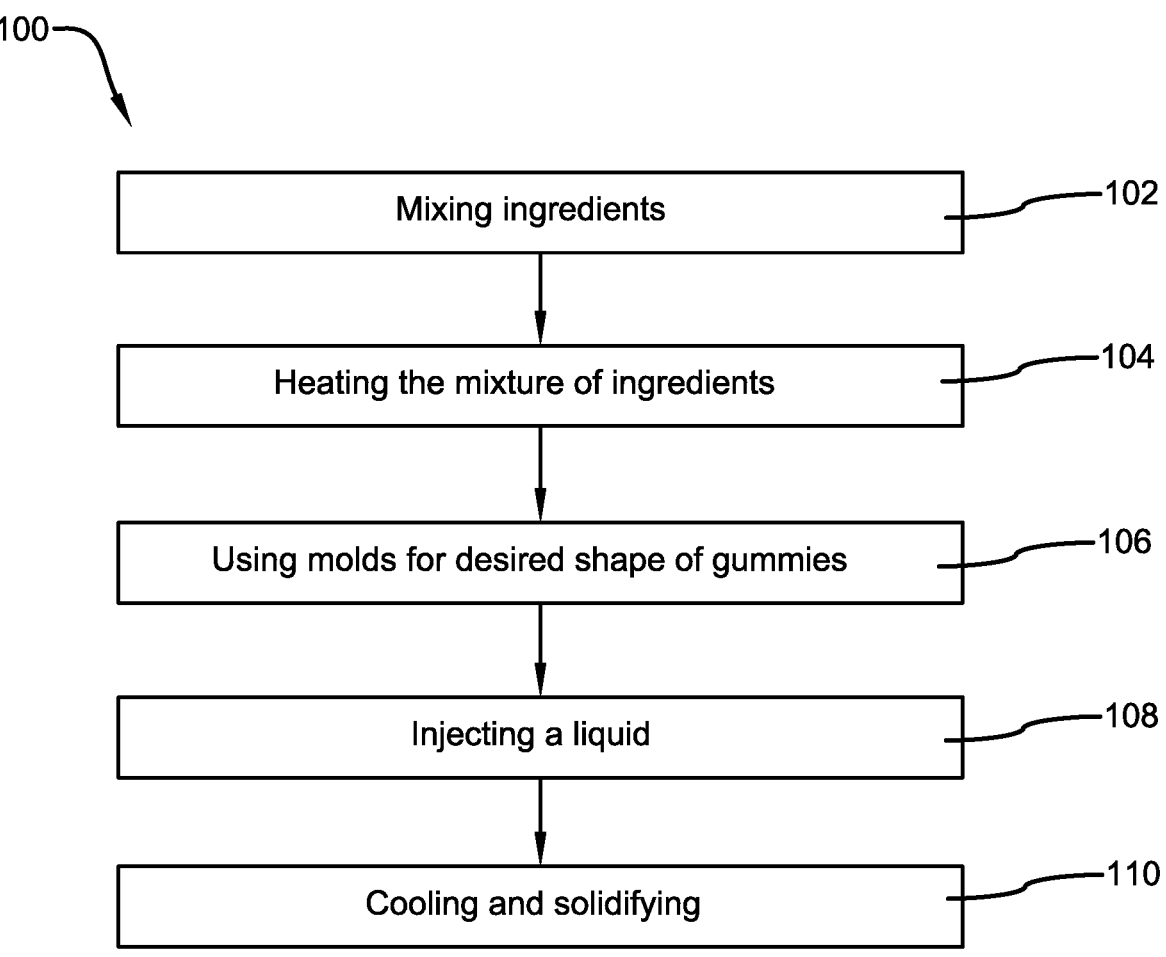
FIG. 1 illustrates a flow chart depicting a process of manufacturing of the liquid-holding edible object of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown.

Thus, in other embodiments, any of the features described herein from different embodiments may be combined.

As noted above, there is a long felt need in the art for an improved gummy that offers a more convenient and mess-free way to consume liquids, beverages, and medicines. There is also a long felt need in the art for a liquid-holding edible gummy or edible chew that prevents overconsumption and enables for more precise dosing of alcohol shots and medications. Additionally, there is a long felt need in the art for a liquid-filled gummy that can serve as an alternative and more palatable way to take medications. Moreover, there is a long felt need in the art for an improved gummy that offers an additional functionality in delivering various liquids stored therein, making the gummy more useful. Further, there is a long felt need in the art for a liquid-filled gummy that can hold any liquid therein. Furthermore, there is a long felt need in the art for a gummy that is edible and holds a liquid inside thereof without any leakage. Finally, there is a long felt need in the art for a gummy filled with liquids that overcomes the problems of consuming beverages and medications in a fun and convenient way.

The present invention, in one exemplary embodiment, is a method for producing an edible gummy or edible chew with a liquid-filled center. The method comprising the steps of mixing ingredients to form a uniform and homogeneous mixture, wherein the ingredients comprise at least gelatin, sweeteners, flavorings, at least one color, heating the mixture in a heating furnace to form a thick and sticky liquid, using different molds for the edible gummy or edible chew, wherein each mold comprises a central cavity for forming a hollow center in the edible object, and pouring the sticky liquid into the mold, injecting a desired liquid, selected from alcohol, medicine, or the like, into the hollow center of the edible object, and cooling and solidifying the filled edible objects, and removing the solidified objects from the molds.

Referring initially to the drawings, FIG. 1 illustrates a flow chart 100 depicting a process of manufacturing of the liquid-holding edible object of the present invention in accordance with the disclosed architecture. Initially, ingredients of the edible object of the present invention are mixed to form a uniform and homogeneous mixture (Step 102). The ingredients include gelatin, sweeteners, flavorings, and at least one color and can be in the form of a powder. In the next step 104, the mixture is heated in a heating furnace to form a thick and sticky liquid. The sticky liquid is heated to a uniform consistency without any lumps. Heating dissolves sugar and hydrates the starch.

Based on the manufacturing process and user requirements, different molds for edible objects of the present invention are used and the sticky liquid is poured in the mold (Step 106). Each mold includes a central cavity for forming a hollow center in the edible object. Thereafter, a desired liquid which can be alcohol, medicine, and the like is injected into the hollow center of the edible object (Step 108). The injection process is performed using an opening in the edible object which is sealed after the edible object is filled with the liquid. Alternatively, a liquid can be added using a gravity split feed system.

In the next step 110, the filled edible objects are cooled and solidified and are removed from the molds. Finally, the edible objects are packaged for distribution and consumption. It will be apparent to a person skilled in the art that preferably the edible object is a gummy and can come in various shapes, sizes, and colors, depending on consumer preferences or marketing strategies. Also, sugar-free options can be provided for providing dietary restrictions to individuals.

The liquid-holding edible object of the present invention can come in different flavors. Table 1 below shows one embodiment of composition of the liquid-holding edible object.

TABLE 1

| Ingredient | % (w/w) |
|---|---|
| Gelatin | 60-80 |
| Sweetener | 2-5 |
| Flavoring | 4-5 |
| Preservative | 1-4 |
| Natural supplement | 4-8 |
| Natural coloring | 5-6 |

Gelatin is the primary ingredient of the liquid-holding edible object. Gelatin is derived from animal collagen and gives the liquid-holding edible gummy or edible chew unique elasticity. For vegetarian or vegan options, plant-based gelling agents like pectin or agar-agar can be used. Sugar, corn syrup, or sugar substitutes such as stevia or xylitol can be used as sweetener. The sweeteners involved may be selected from a wide range of materials including water-soluble sweeteners, water-soluble artificial sweeteners, water-soluble sweeteners derived from naturally occurring water-soluble sweeteners.

Natural or artificial flavorings are added to the gummy. Common flavors may include fruit flavors like strawberry, orange, cherry, and more. Preservatives such as sorbic acid or ascorbic acid is used in the liquid-holding edible gummy or edible chew of the present invention. For providing additional nutrients to a user, natural supplements in the form of different vitamins, minerals, or other nutritional supplements are added to manufacture the gummy. In some embodiments, vitamins can include fat-soluble vitamins such as vitamin A, vitamin D, vitamin E, and vitamin K, and combinations thereof.

Figure 2:
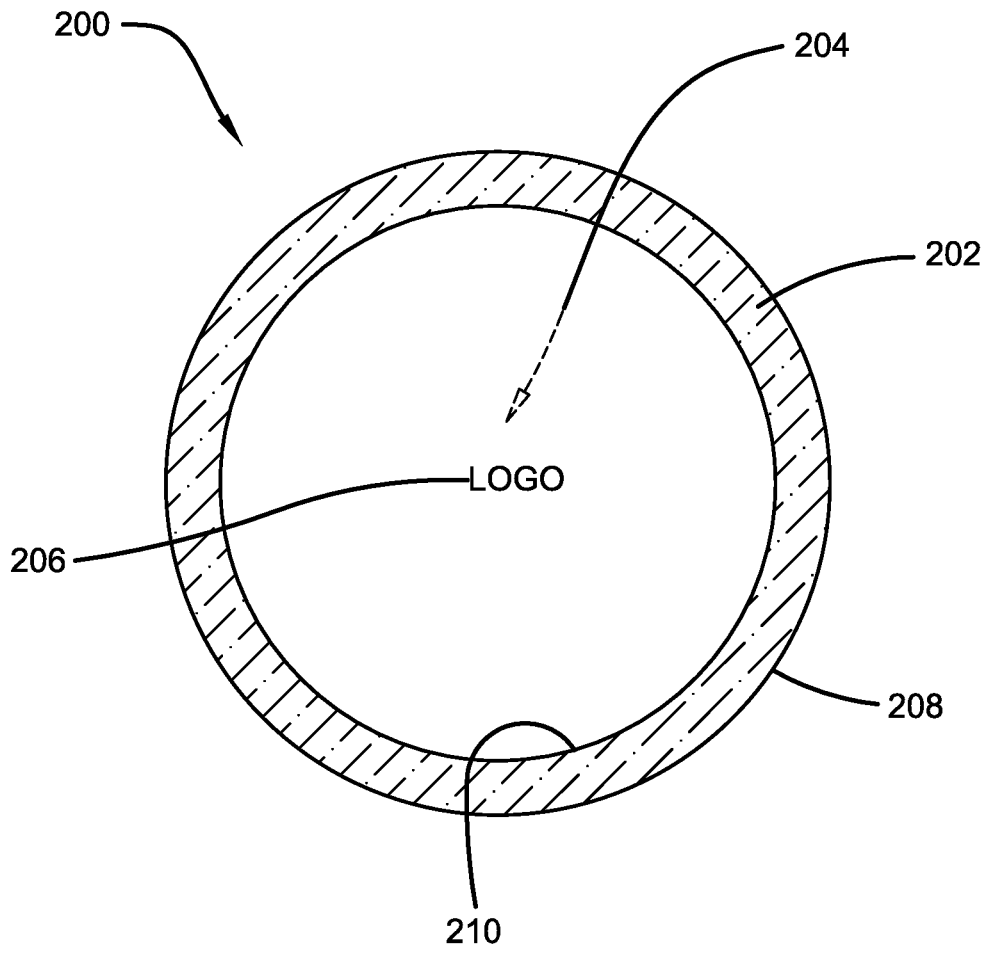
FIG. 2 illustrates a potential embodiment of the liquid-filled gummy of the present invention in accordance with the disclosed structure.

FIG. 2 illustrates a potential embodiment of the liquid-filled gummy of the present invention in accordance with the disclosed structure. The gummy 200 includes a housing 202 made of the composition shown in Table 1 and can be of different shapes and sizes. Further, a central cavity 204 is created inside the housing 202 for accommodating a liquid. The housing 202 can be of different volume for storing medicinal liquid, alcoholic drink, juices, and more. A logo or indicia 206 can be printed on the exterior surface 208 of the housing 202 for branding and marketing purposes. The logo 206 can be 3D printed using an edible ink without affecting the efficacy of the gummy 200.

Water activity is the partial vapor pressure of water in a solution divided by the standard state partial vapor pressure of water and ranges from 0.0 to 1.0. In the field of food science, the standard state is most often defined as pure water at the same temperature. The water activity of the gummy 200 ranges from about 0.2 to about 0.3. As the gummy includes a liquid so the water activity is less than conventional gummies to slow down microbial growth and chemical reactions. The liquid stored in the cavity 204 may permeate through the inner surface 210 of the gummy 200.

In some embodiments, the gummy 200 can provide from about 300 mg calcium to about 2000 mg calcium. In other embodiments, the gummy 200 can provide from about 1 mg to about 5 mg iron. In yet other embodiments, the gummy can provide from about 100 IU to 4000 IU Vitamin D. In pharmacology, the international unit (10) is a unit of measurement for the effect or biological activity of a substance, for the purpose of easier comparison across similar forms of substances.

The gummy 200 of the present invention can come in different flavors such as lemon, orange, lime, grapefruit, a milk flavor, a butter flavor, a cheese flavor, a cream flavor, and a yogurt flavor, a vanilla flavor, a tea flavor, a coffee flavor; or an alcohol, such as a wine, a whisky, a brandy, a rum, a gin, a bourbon, or a liqueur; and more.

Certain terms are used throughout the following description and claims to refer to particular features or components. As one skilled in the art will appreciate, different people may refer to the same feature or component by different names. This document does not intend to distinguish between components or features that differ in name but not structure or function. As used herein "liquid-holding edible object", "liquid-holding edible gummy or edible chew", "edible object", "liquid-filled gummy", and "gummy" are interchangeable and refer to the liquid-holding edible object 200 of the present invention.

Notwithstanding the forgoing, the liquid-holding edible object 200 of the present invention can be of any suitable size and configuration as is known in the art without affecting the overall concept of the invention, provided that it accomplishes the above stated objectives. One of ordinary skill in the art will appreciate that the liquid-holding edible object 200 as shown in the FIG. 2 is for illustrative purposes only, and that many other sizes and shapes of the liquid-holding edible object 200 are well within the scope of the present disclosure. Although the dimensions of the liquid-holding edible object 200 are important design parameters for user convenience, the liquid-holding edible object 200 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A liquid holding edible object comprising:
   a liquid holding chewable having a housing and a cavity,
      wherein said housing comprises a gelatin, a sweetener, a flavoring substance, a preservative, a supplement, and a natural coloring;
   wherein said cavity is enclosed by said housing;
   wherein said cavity has a liquid stored therein;

wherein said liquid comprises a liquid ingredient selected from the group consisting of a water, a juice, an alcohol liquid, a non-alcoholic liquid, and a medicine;

wherein the housing comprises a weight percent of the gelatin of 80%; and further wherein said liquid holding chewable is a gummy having a water activity of 0.3.

2. The edible object of claim 1, wherein said liquid holding chewable comprising a weight percent of said sweetener from 2% to 5%, and further wherein said sweetener is selected from the group consisting of a sugar, a corn syrup, a stevia, and a xylitol.

3. The edible object of claim 2, wherein said liquid holding chewable comprising a weight percent of said flavoring substance from 4% to 5%, and further wherein said flavoring substance is selected from the group consisting of a strawberry, an orange, and a cherry.

4. The edible object of claim 3, wherein said liquid holding chewable comprising a weight percent of said preservative from 1% to 4%.

5. The edible object of claim 4, wherein said liquid holding chewable comprising a weight percent of said supplement from 4% to 8%, and further wherein said supplement is selected from the group consisting of a vitamin A, a vitamin D, a vitamin E, a vitamin K, an iron, and a calcium.

6. The edible object of claim 5, wherein said liquid holding chewable comprising a weight percent of said natural coloring from 5% to 6%.

7. The edible object of claim 1, wherein said liquid further comprises an extract selected from a group consisting of a lemon, an orange, a lime, and a grapefruit.

8. The edible object of claim 1, wherein said liquid further comprises a flavor additive selected from a group consisting of a milk flavor, a butter flavor, a cheese flavor, a cream flavor, a yogurt flavor, a vanilla flavor, a tea flavor, and a coffee flavor.

9. The edible object of claim 1, wherein said alcohol liquid is selected from the group consisting of a wine, a whisky, a brandy, a rum, a gin, a bourbon, and a liqueur.

10. A liquid holding edible object comprising: a liquid holding chewable having a housing and a cavity, wherein said housing comprises a gelatin, a sweetener, a flavoring substance, a preservative, a supplement, and a natural coloring; wherein said cavity is enclosed by said housing; wherein said cavity has a liquid stored therein; and wherein said liquid comprises a liquid ingredient selected from the group consisting of a wine, a whisky, a brandy, a rum, a gin, a bourbon, and a liqueur: wherein the housing comprises a weight percent of the gelatin of 80%; and wherein said liquid holding chewable is a gummy having a water activity of 0.3.

11. The edible object of claim 10, wherein said liquid holding chewable comprising a weight percent of said sweetener from 2% to 5%;

wherein said liquid holding chewable comprising a weight percent of said flavoring substance from 4% to 5%;

wherein said liquid holding chewable comprising a weight percent of said preservative from 1% to 4%;

wherein said liquid holding chewable comprising a weight percent of said supplement from 4% to 8%; and further wherein said liquid holding chewable comprising a weight percent of said natural coloring from 5% to 6%.

12. A method of forming a liquid holding chewable, the method comprising the following steps: mixing a solution of a gelatin, a sweetener, a flavoring substance, a preservative, a supplement, and a natural coloring; heating said solution; pouring said solution into a mold, wherein said mold having a cavity for forming a hollow center in a housing of said chewable; injecting into said hollow center a liquid comprising a liquid ingredient selected from the group consisting of an alcohol and a medicine; cooling and solidifying said chewable; and removing said chewable from said mold; wherein the housing comprises a weight percent of the gelatin of 80%; and further wherein said liquid holding chewable is a gummy having a water activity of 0.3.

13. The method of forming a liquid holding chewable of claim 12, wherein said alcohol is selected from the group consisting of a wine, a whisky, a brandy, a rum, a gin, a bourbon, and a liqueur.

14. The method of forming a liquid holding chewable of claim 12, wherein said chewable comprising a weight percent of said sweetener from 2% to 5%;

wherein said chewable comprising a weight percent of said flavoring substance from 4% to 5%;

wherein said chewable comprising a weight percent of said preservative from 1% to 4%;

wherein said chewable comprising a weight percent of said supplement from 4% to 8%; and further wherein said chewable comprising a weight percent of said natural coloring from 5% to 6%.

15. The method of forming a liquid holding chewable of claim 12, wherein said supplement is selected from the group consisting of a vitamin A, a vitamin D, a vitamin E, a vitamin K, an iron, and a calcium.

16. The method of forming a liquid holding chewable of claim 12, wherein said sweetener is selected from the group consisting of a sugar, a corn syrup, a stevia, and a xylitol.

* * * * *